United States Patent [19]

Lafferty et al.

[11] Patent Number: 5,280,046

[45] Date of Patent: Jan. 18, 1994

[54] METHOD OF TREATING TYPE I DIABETES

[75] Inventors: Kevin Lafferty, Denver, Colo.; Jill A. Panetta, Zionsville, Ind.

[73] Assignee: The University of Colorado Foundation, Inc., Boulder, Colo.

[21] Appl. No.: 659,818

[22] Filed: Feb. 22, 1991

[51] Int. Cl.$^5$ .................. A61K 31/13; A61K 31/135; A61K 31/235; A61K 31/24

[52] U.S. Cl. .................. 514/655; 514/533; 514/538; 514/539; 514/617; 514/650; 514/654

[58] Field of Search .................. 514/655, 628, 61.7, 514/639, 65.4, 65 D, 533

[56] References Cited

U.S. PATENT DOCUMENTS

| 3,043,774 | 7/1962 | Coffield | 252/51.5 |
| 3,305,483 | 2/1967 | Coffield | 252/42.4 |
| 3,489,684 | 1/1970 | O'Shea | 252/51.5 |
| 3,809,761 | 5/1974 | Lerner | 424/330 |
| 3,994,828 | 11/1976 | Zaffaroni | 252/404 |
| 4,116,930 | 9/1978 | Dexter et al. | 260/45.8 N |
| 4,128,664 | 12/1978 | Moore | 424/324 |
| 4,237,165 | 12/1980 | Duhault | 424/308 |
| 4,532,356 | 7/1985 | Everly et al. | 568/315 |
| 4,829,061 | 5/1989 | Wolf et al. | 514/218 |
| 4,948,813 | 8/1990 | Wilkerson | 514/648 |
| 4,959,503 | 9/1990 | Connor et al. | 564/265 |
| 5,011,928 | 4/1991 | Venero et al. | 544/373 |
| 5,087,743 | 2/1992 | Janssen et al. | 562/466 |

FOREIGN PATENT DOCUMENTS

| 42589 | 12/1981 | European Pat. Off. | C08L 65/00 |
| 49981 | 4/1982 | European Pat. Off. | C07C 91/15 |
| 273451 | 7/1988 | European Pat. Off. | C07C 83/10 |
| 276803 | 8/1988 | Fed. Rep. of Germany | C07D 243/08 |
| 1405767 | 9/1975 | United Kingdom | A61K 31/135 |
| 1446781 | 8/1976 | United Kingdom | A61K 31/325 |
| 2146529 | 4/1985 | United Kingdom | A61K 31/135 |
| 2169807A | 7/1986 | United Kingdom | A01N 31/08 |
| 84/00545 | 2/1984 | World Int. Prop. O. | C07D 401/00 |

OTHER PUBLICATIONS

Horii et al., *J. Med. Chem.*, 29(6), 1038-1046 (1986).
Patent Abst. of Japan, vol. 12, No. 467 (C-550) [3314](1988).
*Chemical Abstracts*, 103, 104629y (1985).
*Diabetes Mellitus*, 8th Ed., Eli Lilly and Company, Indianapolis, Ind. pp. 12-17 (1979).
*Chemical Abstracts*, 74, 96312e (1971).
*Derwent Abstracts*, '339971-B (abstracting JA-721730-6-R) (1990).
*Derwent Abstracts*, 20,547 (1990).
*Chemical Abstracts*, 73, 86385w (1970).
*Chemical Abstracts*, 66, 16925d (1967).
*Chemical Abstracts*, 109, 1290447u (1988).
*Chemical Abstracts*, 78, 132326f (1973).
*Chemical Abstracts*, 74, 40916n (1971).
*Chemical Abstracts*, 97, 200429m (1982).
*Chemical Abstracts*, 88, 38847m (1978).
*Chemical Abstracts*, 88, 192135j (1978).
*Chemical Abstracts*, 95, 82029q (1981).
*Chemical Abstracts*, 76, 73628q (1972).
*Chemical Abstracts*, 77, 141203v (1972).
*Chemical Abstracts*, 91, 212411p (1979).
*Chemical Abstracts*, 100, 35563w (1984).
*Chemical Abstracts*, 107, 42468s (1987).
*Derwent Abstracts* 84-076585/13 (1990).
*Derwent Abstracts* 88-193658/28 (1990).
*Chemical Abstracts*, 109, 110014j (1988).
*Derwent Abstracts* 87-076373/11 (1990).
Lafferty et al., *J. of Autoimmun.*, 3 (Suppl.), 75 (1990).
Wang et al., *Transplantation* 46 (Suppl.), 1015 (1988).
Okamoto, *Biomed. Biochim. Acta*, 44(1), 15 (1985).
"The Pathogenesis of Immunologically Mediated Diabetes", *Autoimmunity and the Pathogenesis of Diabetes*, Ginsberg-Fellner et al., ed., Springer-Verlag, New York, pp. 185-205 (1989).
Nomikos et al., *Immunol. Cell Biol.*, 67, 85 (1989).
Wang et al., Abstract from the Keystone Symposium on the Molecular Basis of Oxidative Damage by Leukocytes (Jan. 28-Feb. 1, 1991).

*Primary Examiner*—Jerome D. Goldberg
*Attorney, Agent, or Firm*—John C. Demeter; Leroy Whitaker; Douglas J. Taylor

[57] ABSTRACT

Provided is a method for treating Type I diabetes in mammals utilizing certain phenol and benzamide compounds.

8 Claims, No Drawings

METHOD OF TREATING TYPE I DIABETES

BACKGROUND OF THE INVENTION

Diabetes mellitus is a systemic disease characterized by disorders in the metabolism of insulin, carbohydrates, fats and proteins, and in the structure and function of blood vessels. The primary symptom of acute diabetes is hyperglycemia, often accompanied by glucosuria, the presence in urine of large amounts of glucose, and polyuria, the excretion of large volumes of urine. Additional symptoms arise in chronic or long standing diabetes. These symptoms include degeneration of the walls of blood vessels. Although many different organs are affected by these vascular changes, the eyes appear to be the most susceptible. As such, longstanding diabetes mellitus, even when treated with insulin, is a leading cause of blindness.

There are two recognized types of diabetes. Juvenile onset, or ketosis-prone, diabetes (also known as Type I diabetes) develops early in life, with clinical onset most often occurring before the patient is 18 years of age. Type I diabetes has much more severe symptoms and has a near-certain prospect of later vascular involvement. Control of this type of diabetes is often difficult. The second type of diabetes is adult onset, or ketosis-resistant, diabetes (also known as Type II diabetes). Type II diabetes develops later in life, is milder and has a more gradual onset.

One of the most significant advancements in the history of medical science came in 1922 when Banting and Best demonstrated the therapeutic effects of insulin in diabetic humans. However, even today, a clear picture of the basic biochemical defects of the disease is not known, and diabetes is still a serious health problem. It is believed that two percent or more of the population of the United States is afflicted with some form of diabetes, with 0.1-0.5% afflicted with Type I diabetes.

Type I diabetes is an autoimmune disease which is characterized by a long latent period. Furthermore, the younger the patient is when striken with Type I diabetes, especially if the patient is pre-puberty, the more debilitating the complications resulting from the disease. Accordingly, there is a need for a safe drug which will prevent development of Type I diabetes, or at least prolong onset of the disease for as long a period of time as possible.

It is an object of this invention to provide a method of treating Type I diabetes. More specifically, the invention provides a method of treating Type I diabetes in a mammal, especially a human, which method comprises administering a compound selected from among certain phenols and benzamides of the general formula

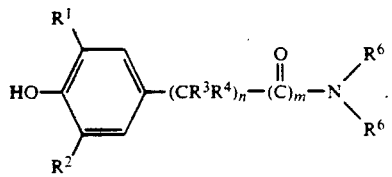

The present method provides for safe and efficacious treatment of Type I diabetes by either preventing development of the disease altogether or by prolonging onset of the disease for as long a period of time as possible, thereby minimizing the disease's concomitant complications.

The method of the present invention employs certain phenols and benzamides of the general formula set forth above. Such compounds are known in the art and have been found to possess various utilities.

U.S. Pat. No. 3,305,483 discloses that certain phenols of the above formula can be used as an antioxidant for various substances such as gasoline, diesel fuel, heating oil, lubricating oil, asphalt, petroleum wax and high molecular weight hydrocarbon polymers. *Chemical Abstracts,* 97, 200429m (1982) teaches that 4-(2-dimethylaminoethyl)-2,6-di-t-butylphenol can be used as an antioxidant for jet aircraft fuel. European Patent Application 42,589 describes the use of various of the above phenols as antioxidents for polymeric norbornene type polymeric materials.

*Chemical Abstracts,* 88, 38847m (1978) discloses that 2,6-di-t-butyl-4-[N,N-bis(2-hydroxyethyl)aminomethyl]phenol can be used to increase the heat resistance of certain fibers. *Chemical Abstracts,* 88, 192135j (1978) teaches that 1-phenyl-4-(3,5-di-t-butyl-4-hydroxybenzyl)piperazine is a noncolorizing thermostabilizer for stress-stable polystyrene. 2-(3,5-Di-t-butyl-4-hydroxyphenyl)ethylmethylamine is described as being useful for improving the lightfastness of dyed polyester fibers in *Chemical Abstracts,* 76, 73628q (1972).

*Chemical Abstracts,* 77, 141203v (1972) teaches that 3-(dimethylamino)propylaminobis(4-methylene-2,6-di-t-butylphenol can be used to improve the aging resistance of diene rubber. *Chemical Abstracts,* 91 12411p (1979) describes a 1:1 pyrocatechol/4-[(dimethylamino)methyl]-2,6-di-t-butylphenol complex which deactivates transition metals in rubber. N,N-dimethyl-3,5-di-t-butyl-4-hydroxybenzylamine is disclosed to be an effective polymerization inhibitor for styrene in *Chemical Abstracts,* 100, 35563w (1984). *Chemical Abstracts,* 107, 42468s (1987) discloses that 3-(4-hydroxy-3,5-di-t-butylphenyl)-1-aminopropane acetate or N-(4-hydroxy-3,5-di-t-butylbenzyl)-N-(β-aminoethyl)piperazine hydrochloride can be used to modify cation exchange resins so as to reduce the diffusive permeability of the resin membrane and increase its sodium ion transport properties.

Several of the phenols and benzamides of the general formula set forth above have also been found to possess various pharmacological activities. U.S. Pat. No. 3,809,761 discloses that certain of the above phenols can be used to reduce mammalian plasma lipid levels. *Chemical Abstracts,* 73, 86385w (1970) and *Chemical Abstracts,* 66, 16925d (1967) teach that certain of the above phenols have antitumor activity. *Chemical Abstracts,* 74, 96312e (1971) discloses that (4-hydroxy-3,5-di-t-butylbenzyl)methylamine hydrochloride increases the antioxidative activity of liver lipids, thereby increasing liver tissue regeneration following a partial hepatectomy. N-methyl-3,5-di-t-butyl-4-hydroxybenzylamine is said to be able to increase the rate of blood deoxygenation in *Chemical Abstracts,* 78, 132326f (1973). Chemical Abstracts, 109, 110014j (1988) and *Derwent Abstracts,* 87-076373/11 teach that certain of the phenols used in the method of the present invention are useful as antiinflammatory, antirheumatic, anti-allergenic, analgesic, diuretic, platelet agglutination-inhibiting (antithrombotic), hypotensive and antilipaemic agents and are lipoxygenase inhibitors. Finally, *Chemical Abstracts,* 109, 129047u (1988) discloses that certain benzamides of the above formula are useful for treating epilepsy and high blood pressure.

The phenols and benzamides employed in the method of the present invention have not heretofore been used to treat Type I diabetes in mammals. The known activities of such compounds, as set forth above, in no way suggest the method of the present invention. Accordingly, an object of the present invention is to provide a new pharmacological use for certain known phenols and benzamides.

Other objects, features and advantages of the present invention will become apparent from the subsequent description and the appended claims.

SUMMARY OF THE INVENTION

The present invention provides a method for treating Type I diabetes in a mammal suffering from such disease, or susceptible to such disease, which comprises administering to said mammal an effective amount of a compound, or pharmaceutically acceptable salt thereof, of formula I

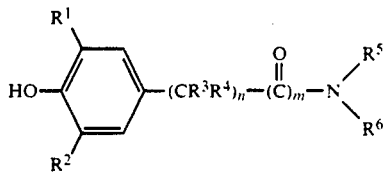

wherein:

$R^1$ and $R^2$ are each independently hydrogen, $C_1$-$C_6$ alkyl, $C_1$-$C_6$ alkoxy or

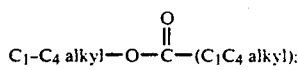

$R^3$ and $R^4$ are each independently hydrogen or $C_1$-$C_4$ alkyl;

n is an integer from 0 to 4, both inclusive;

m is 0 or 1; and $R^5$ and $R^6$ are defined to be one of the following:

A) $R^5$ and $R^6$ are each independently hydrogen, $C_1$-$C_8$ alkyl, $C_3$-$C_8$ cycloalkyl, $C_2$-$C_8$ alkenyl, $C_2$-$C_8$ alkynyl, $(CH_2)_q OR^7$, $-(CH_2)_q N(R^7R^8)$, $-(CH_2)_q SR^7$, $-(CH_2)_r$ napthyl or

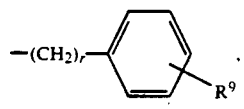

where q is an integer from 1 to 6, both inclusive, $R^7$ and $R^8$ are each independently hydrogen or $C_1$-$C_4$ alkyl, $R^9$ is hydrogen, halo, $C_1$-$C_4$ alkyl, trifluoromethyl, hydroxy, amino, $C_1$-$C_4$ alkylamino, di($C_1$-$C_4$ alkyl)amino, phenylamino or diphenylamino, and r is an integer from 0 to 4, both inclusive;

B) one of $R^5$ or $R^6$ is as defined in (A) above and the other is

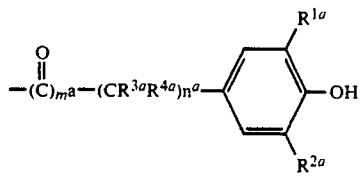

wherein $m^a$, $n^a$, $R^{1a}$, $R^{2a}$, $R^{3a}$ and $R^{4a}$ are the same substituent as m, n, $R^1$, $R^2$, $R^3$ and $R^4$, respectively; or C) $R^5$ and $R^6$, taken together with the nitrogen atom to which they are attached, form

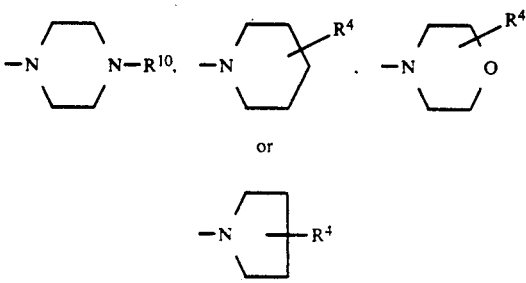

where $R^4$ is as defined above and $R^{10}$ is hydrogen, $C_1$-$C_4$ alkyl,

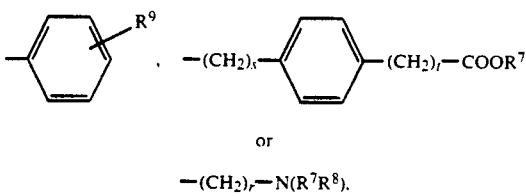

or $-(CH_2)_r-N(R^7R^8)$.

where $R^7$, $R^8$, $R^9$ and r are as defined above and s and t are each independently an integer from 0 to 4, both inclusive.

DETAILED DESCRIPTION OF THE INVENTION

As used herein, the term "$C_1$-$C_8$ alkyl" refers to straight and branched chain aliphatic radicals of 1 to 8 carbon atoms, both inclusive, such as methyl, ethyl, propyl, isopropyl, butyl, isobutyl, sec-butyl, tert-butyl, n-pentyl, isopentyl, n-hexyl, isohexyl, n-heptyl, n-octyl, isooctyl and the like. The term "$C_1$-$C_8$ alkyl" includes within its definition the terms "$C_1$-$C_6$ alkyl" and "$C_1$-$C_4$ alkyl".

The term "$C_1$-$C_6$ alkoxy" refers to the alkyl radicals of 1 to 6 carbon atoms, both inclusive, attached to the remainder of the molecule by oxygen and includes methoxy, ethoxy, propoxy, isopropoxy, butoxy, isobutoxy, sec-butoxy, tert-butoxy, pentoxy, hexoxy and the like.

The term "$C_2$-$C_8$ alkenyl" refers to straight and branched chain radicals of 2 to 8 carbon atoms, both inclusive, having a double bond. As such, the term includes ethylene, propylene, isopropylene, 1-butene, 2-butene, 2-methyl-1-propene, 1-pentene, 2-pentene, 2-methyl-2-butene, 1-heptene, 1-octene and the like. The term "$C_2$-$C_8$ alkenyl" includes within its definition the term "$C_2$-$C_6$ alkenyl".

The term "$C_2$-$C_8$ alkynyl" refers to straight and branched chain radicals of 2 to 8 carbon atoms, both inclusive, having a triple bond. As such, the term includes acetylene, propyne, 1-butyne, 2-butyne, 1-pentyne, 2-pentyne, 3-methyl-1-butyne, 1-hexyne, 2-hexyne, 3-hexyne, 1-heptyne, 1-octyne and the like. The term "$C_2$-$C_8$ alkynyl" includes within its definition the term "$C_2$-$C_6$ alkynyl".

The term "$C_3$-$C_8$ cycloalkyl" refers to saturated alicyclic rings of 3 to 8 carbon atoms, both inclusive, such as cyclopropyl, methylcyclopropyl, cyclobutyl, cyclopentyl, cyclohexyl, cyclooctyl and the like.

The term "naphthyl" refers to a 1-naphthyl or 2-naphthyl moiety.

The term "halo" refers to bromo, chloro, fluoro and iodo.

The pharmaceutically acceptable salts of the compounds of formula I are also useful in treating Type I diabetes. Accordingly, such salts are included within the scope of the method of this invention.

The term "pharmaceutically acceptable salt", as used herein, refers to salts of the compounds of formula I which are substantially non-toxic to living organisms. Typical pharmaceutically acceptable salts include those salts prepared by reaction of the free base form of the compound of formula I with a pharmaceutically acceptable mineral or organic acid. Pharmaceutically acceptable mineral or organic acids commonly employed to form such salts include inorganic acids such as hydrochloric, hydrobromic, hydroiodic, nitric, sulfuric and phosphoric acid, as well as organic acids such as paratoluenesulfonic, methanesulfonic, oxalic, parabromophenylsulfonic, carbonic, succinic, citric, benzoic, acetic, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, hydrochloride, hydrobromide, hydroiodide, acetate, nitrate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, $\beta$-hydroxybutyrate, glycollate, tartrate, methanesulfonate, propanesulfonate, naphthalene-2-sulfonate, p-toluenesulfonate, mandelate and the like salts. Preferred pharmaceutically acceptable acid addition salts include those formed with mineral acids such as hydrochloric acid and nitric acid, and those formed with organic acids such as acetic acid, maleic acid, and methanesulfonic acid.

Depending upon the definitions of $R^3$, $R^4$ and n, the compounds of formula I may exist in various isomeric forms. This invention is not related to any particular isomer but includes all possible individual isomers and racemates. Unless otherwise indicated, all compounds named herein are intended to exist as racemic mixtures.

The phenols and benzamides of formula I are either known in the art or may be prepared by any of a number of well-known procedures. For example, many of the phenols of formula I may be prepared using Mannich reaction conditions. Such conditions are well known and essentially consist of condensing ammonia or a primary or secondary amine, with an aldehyde (especially formaldehyde) and an appropriately-substituted phenol.

The phenols of formula I may also be prepared using reductive amination. Such reaction entails reacting an appropriately substituted p-hydroxyphenylaldehyde (such as p-hydroxybenzaldehyde), or a ketone derivative thereof, with a primary amine so as to form an imine, which compound is then reduced with a reducing agent such as lithium aluminum hydride, sodium borohydride, sodium cyanoborohydride, hydrogen and a catalyst, or the like, to provide the corresponding amine. Reductive amination is an especially useful method for preparing the "dimer" compounds of formula I, i.e., those compounds wherein one of $R^5$ or $R^6$ is

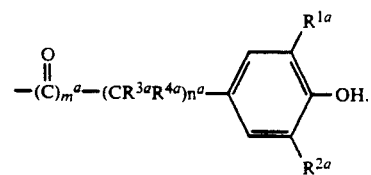

Such compounds are readily prepared by reductive amination provided the primary amine substrate is employed in a quantity sufficient to provide an amine/aldehyde or ketone mole ratio of less than about 3:1. If amine/aldehyde or ketone mole ratios of greater than about 3:1 are employed, the "monomer" (compounds wherein neither $R^5$ nor $R^6$ are as set forth immediately above) rather than the "dimer" are preferentially obtained.

Many of the benzamides of formula I may be prepared by reacting an appropriately substituted p-hydroxyphenylcarboxylic acid, such as p-hydroxybenzoic acid or p-hydroxybenzylcarboxylic acid, or a reactive derivative thereof (such as an acid chloride), with a primary or secondary amine to form the desired benzamide. When a free carboxylic acid substrate is employed, the reaction is usually carried out in the presence of a dehydrating agent such as 1,3-dicyclohexylcarbodiimide (DDC) or N,N-carbonyldiimidazole. The benzamide thus produced may be used in the method of the present invention or, alternatively, may be converted to a phenol of formula I by reduction of the amide functionality using a reducing agent such as lithium aluminum hydride, diborane or catalytic hydrogenation.

Phenols and benzamides of formula I wherein $R^1$ are/or $R^2$ are $C_2$-$C_6$ alkyl may also be prepared using Friedel-Crafts alkylation conditions. Such reaction conditions are well-known and consist essentially of reacting a non-substituted or mono-substituted phenol or p-hydroxybenzamide of formula I (i.e., at least one of $R^1$ and $R^2$ must be hydrogen) with a $C_2$-$C_6$ alkene in the presence of a proton acid such as sulfuric acid.

A group of preferred compounds of formula I which are particularly suited for the method o the present invention are those compounds wherein m and n are as defined above with the proviso that both m and n cannot be zero. Of these preferred compounds, particularly preferred compounds for use in the method of the present invention are those compounds wherein $R^1$, $R^2$, $R^3$ and $R^4$, are as defined previously and $R^5$ and $R^6$ are defined to be one of the following:

A) $R^5$ and $R^6$ are each independently hydrogen, $C_1$-$C_6$ alkyl, $C_2$-$C_6$ alkenyl, $C_2$-$C_6$ alkynyl, —$(CH_2)_q$OH, —$(CH_2)_q$NH$_2$, —$(CH_2)_q$NH($C_1$-$C_4$ alkyl), —$(CH_2)_q$N($C_1$-$C_4$ alkyl)$_2$, —$(CH_2)_q$S($C_1$-$C_4$ alkyl) or

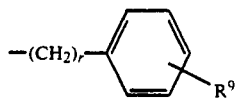

where q and r are both as previously defined;

B) one of $R^5$ and $R^6$ is as defined in (A) immediately above and the other is

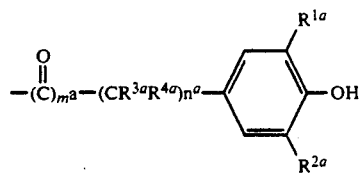

wherein $m^a$, $n^a$, $R^{1a}$, $R^{2a}$, $R^{3a}$, and $R^{4a}$ are the same substituent as m, n, $R^1$, $R^2$, $R^3$, and $R^4$, respectively; or C) $R^5$ and $R^6$, taken together with the nitrogen atom to which they are attached, form

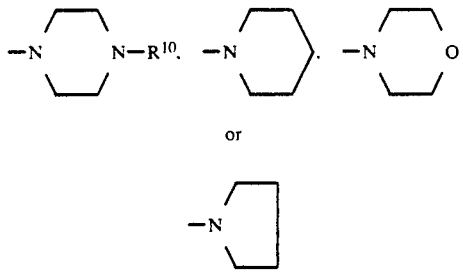

wherein $R^{10}$ is hydrogen or $C_1$–$C_4$ alkyl.

In this particularly preferred group of compounds, the following substituents are especially preferred.

i) $R^1$ and $R^2$ are each independently $C_1$–$C_4$ alkyl;
ii) one of $R^1$ and $R^2$ is 1,1-dimethylethyl and the other is $C_1$–$C_4$ alkyl;
iii) one of $R^1$ and $R^2$ is 1,1-dimethylethyl and the other is methyl;
iv) $R^1$ and $R^2$ are both 1,1-dimethylethyl;
v) one of $R^1$ and $R^2$ is 1,1-dimethylethyl and the other is hydrogen;
vi) one of $R^3$ and $R^4$ is hydrogen and the other is hydrogen or $C_1$–$C_4$ alkyl;
vii) one of $R^3$ and $R^4$ is hydrogen and the other is methyl;
viii) $R^3$ and $R^4$ are both hydrogen;
ix) n is 0 and m is 1;
x) n is 1 and m is 0;
xi) n is 2 and m is 0;
xii) $R^5$ and $R^6$ are each independently hydrogen or $C_1$–$C_6$ alkyl;
xiii) $R^5$ and $R^6$ are each independently hydrogen or $C_1$–$C_4$ alkyl;
xiv) $R^5$ and $R^6$ are each independently hydrogen or methyl;
xv) $R^5$ and $R^6$ are each independently hydrogen or ethyl;
xvi) $R^5$ and $R^6$ are each independently hydrogen or n-propyl;
xvii) $R^5$ and $R^6$ are each independently hydrogen or n-butyl;
xviii) $R^5$ and $R^6$ are each independently hydrogen or t-butyl;
xix) $R^5$ and $R^6$ are both methyl;
xx) $R^5$ and $R^6$ are both ethyl;
xxi) $R^5$ and $R^6$ are both n-propyl;
xxii) $R^5$ and $R^6$, taken together with the nitrogen atom to which they are attached form

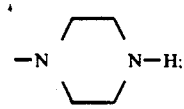

xxiii) $R^5$ and $R^6$, taken together with the nitrogen atom to which they are attached, form

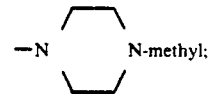

xxiv) $R^5$ and $R^6$, taken together with the nitrogen atom to which they are attached, form

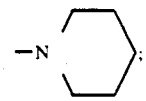

xxv) $R^5$ and $R^6$, taken together with the nitrogen atom to which they are attached, form

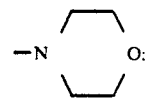

xxvi) $R^5$ and $R^6$, taken together with the nitrogen atom to which they are attached, form

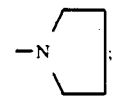

xxvii) pharmaceutically acceptable salts of any of the above compounds.

Especially preferred compounds which can be used in the method of the present invention are compounds of the formula

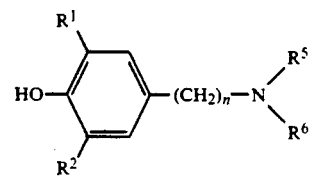

wherein $R^1$ and $R^2$ are either both 1,1-dimethylethyl or one of $R^1$ and $R^2$ is hydrogen or methyl and the other is 1,1-dimethylethyl, n is an integer from 1 to 4, both inclusive, and $R^5$ and $R^6$ are each independently hydrogen or $C_1$–$C_4$ alkyl or, when taken together with the nitrogen atom to which they are attached, form

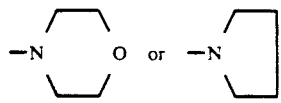

The most preferred compounds which may be used in the method of treating Type I diabetes of the present invention are 4-[(dimethylamino)methyl]-2,6-bis(1,1-dimethylethyl)phenol, 4-[(ethylamino)methyl]-2,6-bis (1,1-dimethylethyl)phenol and the pharmaceutically acceptable salts thereof.

Further typical examples of compounds of formula I which are useful in treating Type I diabetes, according to this invention, include:

4-[(dimethylamino)methyl]-2,6-bis(1,1-dimethylethyl)-phenol
4-[(dimethylamino)methyl]-2,6-bis(1,1-dimethylethyl)-phenol hydrochloride
4-[(dimethylamino)methyl]-2,6-bis(1,1-dimethylethyl)-phenol methanesulfonate
N,N-dimethyl-3,5-bis(1,1-dimethylethyl)-4-hydroxybenzamide
4-{[N-methyl-N-(4-hydroxy-3,5-bis(1,1-dimethylethyl)-benzyl)amino]methyl}-2,6-bis(1,1-dimethylethyl)-phenol
4-{[N-methyl-N-(4-hydroxy-3,5-bis(1,1-dimethylethyl)-benzyl)amino]methyl}-2,6-bis(1,1-dimethylethyl)-phenol hydrochloride
4-[2-(dimethylamino)ethyl]-2,6-bis(1,1-dimethylethyl)-phenol
4-[2-(dimethylamino)ethyl]-2,6-bis(1,1-dimethylethyl)-phenol hydrochloride
4-[2-(methylamino)ethyl]-2,6-bis(1,1-dimethylethyl)-phenol hydrochloride
4-(4-morpholinylmethyl)-2,6-bis(1,1-dimethylethyl)-phenol
4-(4-morpholinylmethyl)-2,6-bis(1,1-dimethylethyl)-phenol hydrochloride
4-(1-pyrrolidinomethyl)-2,6-bis(1,1-dimethylethyl)-phenol
4-(1-pyrrolidinomethyl)-2,6-bis(1,1-dimethylethyl)-phenol hydrochloride
4-[(N-ethyl-N-methylamino)methyl]-2,6-bis(1,1-dimethylethyl)phenol methanesulfonate
4-[(diethylamino)methyl]-2,6-bis(1,1-dimethylethyl)-phenol hydrochloride
4-[(dipropylamino)methyl]-2,6-bis(1,1-dimethylethyl)-phenol hydrochloride
4-[(methylamino)methyl]-2,6-bis(1,1-dimethylethyl)-phenol hydrochloride
4-[(ethylamino)methyl]-2,6-bis(1,1-dimethylethyl)-phenol hydrochloride
4-[(ethylamino)methyl]-2,6-bis(1,1-dimethylethyl)-phenol nitrate
4-{[(1,1-dimethylethyl)amino]methyl}-2,6-bis(1,1-dimethylethyl)phenol hydrochloride
4-[2-(methylamino)ethyl]-2-(1,1-dimethylethyl)phenol hydrochloride
4-[(dimethylamino)methyl]-2-(1,1-dimethylethyl)-6-methylphenol
4-[(n-propylamino)methyl]-2,6-bis(1,1-dimethylethyl)-phenol hydrochloride
4-[1-(ethylamino)ethyl]-2,6-bis(1,1-dimethylethyl)-phenol hydrochloride
4-[(dipropylamino)methyl]-2,6-bis(1,1-dimethylethyl)-phenol
4-[(N-ethyl-N-methylamino)methyl]-2,6-bis(1,1-dimethylethyl)phenol
4-[(diethylamino)methyl]-2,6-bis(1,1-dimethylethyl)-phenol
4-[(n-propylamino)methyl]-2-ethylphenol
4-[(dimethylamino)methyl]-2,6-dimethylphenol
4-[(N-n-butyl-N-cyclohexylamino)methyl]-2,6-bis(1,1-dimethylethyl)phenol acetate
4-[3-(dicycloheptylamino)propyl]-2,6-diethoxyphenol
4-[2-(diphenylamino)ethyl]-2,6-diethylphenol tartrate
4-{4-[N-hexyl-N-(3-butene)amino]butyl}-2-methoxyphenol
4-{[(2-(dimethylamino)ethyl)amino]methyl}-2,6-diisopropylphenol hydrobromide
4-{[N-ethyl-N-(3-phenylpropyl)amino]methyl}-2-ethyl-6-methylphenol
4-{2-[N-cyclopentyl-N-(aminomethyl)amino]ethyl}-2-(1,1-dimethylethyloxy)phenol
4-{2-[(2-hydroxyethyl)amino]ethyl-2-propylphenol citrate
4-(1-piperidinylmethyl)-2,6-diethylphenol
4-(1-piperidinylmethyl)-2,6-diethylphenol hydrobromide
4-[1-(3-ethyl)piperidinylmethyl]-2,6-dimethoxyphenol
4-[4-(2-methyl)morpholinylmethyl]-2-(1,1-dimethylethyl)phenol phosphate
4-[2-(1-piperazinyl)ethyl]-2-n-butyl-6-methylphenol
4-{3-[1-(4-methyl)piperazinyl]propyl}-2-ethoxy-6-isopropylphenol toluenesulfonate
N-isopropyl-N-cyclobutyl-3,5-dimethyl-4-hydroxybenzamide hydrochloride
N-(methylthiomethyl)-3-(1,1-dimethylethyl)-4-hydroxybenzamide decanoate
N,N-diethylene-3-ethoxy-4-hydroxy-5-isopropylbenzamide maleate
(−)-4-[1-(methylamino)ethyl]-2,6-diethylphenol
(+)-4-[1-(diethylamino)butyl-2-methoxyphenol lactate
(+)-4-[1-methyl-2-(cyclohexylamino)butyl]-2-isopropyl-6-methylphenol sulfate
(−)-4-{1-[1-(4-n-propyl)piperazinyl]ethyl}-2-ethoxy-6-methoxyphenol hydroxybenzoate
(−)-4-[1-(2-phenylethylamino)propyl]-2,6-bis(1,1-dimethylethyl)phenol sulfite
N,N-diethyl-[3-(3,5-diethyl-4-hydroxyphenyl)propyl]-carboxamide
N-octyl-[(3-isopropyl-4-hydroxyphenyl)methyl]carboxamide heptanoate
N-methyl-N-n-propyl-[2-(3,5-diisobutoxy-4-hydroxyphenyl)ethyl]carboxamide formate
N-2-chlorophenyl-3,5-bis(1,1-dimethylethyl)-4-hydroxybenzamide
4-[(isopropylamino)methyl]-2,6-bis(1,1-dimethylethyl)-phenol
4-[(isopropylamino)methyl]-2,6-bis(1,1-dimethylethyl)-phenol hydrochloride Insulin independent diabetes mellitus (Type I diabetes) results from an immunological attack on pancreatic islet tissue, a process thought to be a form of autoimmunity. Islet damage in situ results in the development of clinical diabetes. This process develops spontaneously in non-obese diabetic (NOD) mice and can be accelerated in diabetes prone animals by treatment of these animals with cyclophosphamide. When islet tissue is grafted to spontaneously diabetic animals, the grafted tissue is also subject to this "autoimmune" attack. Thus, agents that modify this immunological process can be assayed either by their ability to inhibit the development of diabetes, or by their capacity to prevent disease recurrence in grafted tissue.

As noted previously, the compounds of formula I are useful for treating Type I diabetes in mammals. Such activity was demonstrated by testing the capacity of the compounds of formula I to prevent disease recurrence when islet tissue is grafted to spontaneously diabetic animals and also to prevent cyclophosphamide induced diabetes in diabetes prone NOD mice. Such tests, and the results obtained therefrom, are reported below.

Disease Recurrence Model

Islets (450) from four female BALB/c mice were isolated and cultured using the procedure described by Prowse et al., *Methods In Diabetes Research*, S. L. Pohl, ed., John Wiley and Sons, Inc., New York, N.Y., 253-269 (1984). Nine clusters (equivalent to 450 islets) of cultured BALB/c islets were transplanted under the kidney capsule of female diabetic NOD recipient mice. One day prior to transplantation the test animals were fed a diet consisting of test compound in vehicle or vehicle alone (control). Administration of such a diet continued for the next 29 days. If diabetes re-occurred in the islet graft, the test animal was sacrificed on day 14 and the graft was removed for histological examination. However, if diabetes did not re-occur the test animal was switched to its regular diet after a total of 30 days of test diet administration (test day number 28). Monitoring of test animals continued until the animal had two consecutive blood glucose readings out of normal range. At that time the animal was sacrificed. The results of such testing was reported in Table I, below.

In Table I, Column 1 discloses the type of test diet administered (test compound or control), while Column 2 discloses the amount of test compound (weight %) administered in the animal's diet. Column 3 describes the number of animals tested. Finally, Column 4 discloses the islet survival time, in days, of each cultured BALB/c islet graft after administration of test compound or control.

TABLE I

| | Protection of the Cultured BALB/c Islet Graft | | |
|---|---|---|---|
| Compound/Control | % Test Compound in Diet (wgt %) | No. of Test Animals | Survival Time (days) |
| Control | — | 12 | 0.5,0,0,0,0,0,0, 0,0,3,3 |
| 4-[(dimethylamino)-methyl]-2,6-bis(1,1-dimethylethyl)phenol | 0.1 | 11 | 28,9,22,22,6,33, 36,14,2,7,20* |

*Indicates statistical probability p ≤ 0.05

Inhibition of Cyclophosphamide Induced Diabetes

Male NOD mice (Taconic Farm) from 90 to 120 days of age were given a 250 mg/kg dose of cyclophosphamide intraperitoneally (day 0). One day prior to cyclophosphamide treatment the test animals were fed a diet consisting of test compound in vehicle (0.1% by weight test compound in vehicle) or vehicle alone (control). Administration of such diet continued for a period of 21 days while the test animals were screened for diabetes as determined by blood glucose measurement (diabetes was defined as a blood glucose level of greater than 10 mmol/l for two consecutive readings two days apart). Each animal was sacrificed either two days after it became diabetic or 21 days after cyclophosphamide treatment. The results of such testing are reported in Table II, below. For the results reported in Table II, a Fisher exact test was performed to test for significant differences between the test compound group of animals and the control animals.

In Table II, Column 1 discloses the type of test diet administered (test compound or control), while Column 2 discloses the amount of test compound (weight %) administered in the animal's diet. Column 3 discloses the proportion of animals which turned diabetic during the test. Finally, Column 4 discloses the mean number of days that it took for the animals that became diabetic to become diabetic.

TABLE II

| Effect of Test Compound on Cyclophosphamide Induced Diabetes | | |
|---|---|---|
| Compound/Control | Proportion Turning Diabetic (# diabetic/ total # tested) | Mean Days to Diabetes |
| Control | 33/50 | 12.0 ± 1.3 |
| 4-[(dimethylamino)-methyl]-2,6-bis(1,1-dimethylethyl)phenol | 12/18 | 15.7 ± 2.4* |

*Indicates statistical probability p ≤ 0.05

The data in Tables I and II establish that the compounds used in the method of the present invention can be used to treat Type I diabetes. In particular, the data in Tables I and II establish that the compounds used in the method of the present invention can prevent disease recurrence in islet graft transplants. Furthermore, where the compounds failed to prevent development of diabetes, the onset of diabetes was significantly delayed relative to the onset of diabetes in the control group. Such delay, even though diabetes is not prevented, is beneficial since the younger the patient's age when striken with Type I diabetes, the more debilitating the complications resulting from the disease.

The method of the present invention comprises administering to a mammal suffering from, or susceptible to, Type I diabetes an effective amount of one or more of the compounds of formula I. Administration may be done either therapeutically or prophylactically. For purposes of the present application, the term "effective amount" refers to any amount of a compound of formula I sufficient to achieve the desired therapeutic or prophylatic effect.

The compounds can be administered by a variety of routes including the oral, rectal, transdermal, subcutaneous, intravenous, intramuscular or intranasal routes. The oral and intravenous routes of administration are preferred. No matter what route of administration is chosen, such administration is accomplished by means of pharmaceutical compositions which are prepared by techniques well known in the pharmaceutical sciences.

In making the pharmaceutical compositions, one or more active ingredients will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions may be formulated so as to provide rapid, sustained or delayed release of the active ingredient after administration to the patient by employing procedures well known in the art.

The compositions are formulated, preferably in a unit dosage form, such that each dosage contains from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic or prophylactic effect, in association with one or more suitable pharmaceutical diluents, excipients or carriers.

The compounds used in the method of the present invention are effective over a wide dosage range for treating Type I diabetes. Thus, as used herein, the term "effective amount" refers to a dosage range of from about 0.001 to about 200 mg/kg of body weight per day. In the treatment of adult humans, the range of about 0.1 to about 50 mg/kg, in single or divided doses, is preferred. However, it will be understood that the amount of the compound actually administered will be determined by a physician, in the light of the relevant circumstances including the choice of compound to be administered, whether prophylactic or therapeutic effect is desired, the chosen route of administration, the age, weight, and response of the individual patient, and the severity of the patient's symptoms, and therefore the above dosage ranges are not intended to limit the scope of the invention in any way.

The following formulation examples may employ as active ingredients any of the compounds of formula I. The examples are illustrative only and are not intended to limit the scope of the invention in any way.

EXAMPLE 1

Hard gelatin capsules are prepared using the following ingredients:

|  | Quantity (mg/capsule) |
| --- | --- |
| 4-[dimethylamino)methyl]-2,6-bis(1,1-dimethylethyl)-phenol hydrochloride | 250 |
| Starch dried | 200 |
| Magnesium stearate | 10 |

The above ingredients are mixed and filled into hard gelatin capsules in 460 mg quantities.

EXAMPLE 2

A tablet formula is prepared using the ingredients below:

|  | Quantity (mg/tablet) |
| --- | --- |
| 4-[(ethylamino)methyl]-2,6-bis(1,1-dimethylethyl)-phenol hydrochloride | 250 |
| Cellulose, microcrystalline | 400 |
| Silicon dioxide, fumed | 10 |
| Stearic acid | 5 |

The components are blended and compressed to form tablets each weighing 665 mg.

EXAMPLE 3

An aerosol solution is prepared containing the following components:

|  | Weight % |
| --- | --- |
| 4-[2-(dimethylamino)ethyl]-2,6-bis(1,1-dimethylethyl)-phenol | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

EXAMPLE 4

Tablets each containing 60 mg of active ingredient are made up as follows:

| | |
| --- | --- |
| 4-[(dimethylamino)methyl]-2,6-bis(1,1-dimethylethyl)-phenol | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°-60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed by a tablet machine to yield tablets each weighing 150 mg.

EXAMPLE 5

Capsules each containing 80 mg of medicament are made as follows:

| | |
| --- | --- |
| 4-[(methylamino)methyl]-2,6-bis(1,1-dimethylethyl)-phenol hydrochloride | 80 mg |
| Starch | 59 mg |
| Microcrystalline cellulose | 59 mg |

| | |
|---|---|
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

EXAMPLE 6

Suppositories each containing 225 mg of active ingredient are made as follows:

| | |
|---|---|
| 4-[2-(methylamino)ethyl]-2,6-bis(1,1-dimethylethyl)-phenol hydrochloride | 225 mg |
| Saturated fatty acid glycerides to | 2.000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 7

Suspensions each containing 50 mg of medicament per 5 ml dose are made as follows:

| | |
|---|---|
| 4-[(dimethylamino)methyl]-2,6-bis(1,1-dimethylethyl)-phenol | 50 mg |
| Sodium carboxymethylcellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

EXAMPLE 8

Capsules each containing 150 mg of medicament are made as follows:

| | |
|---|---|
| 4-[(ethylamino)methyl]-2,6-bis(1,1-dimethylethyl)-phenol | 150 mg |
| Starch | 164 mg |
| Microcrystalline cellulose | 164 mg |
| Magnesium stearate | 22 mg |
| Total | 500 mg |

The active ingredient, cellulose, starch and magnesium stearate are blended, passed through a No. 45 mesh U.S. sieve, and filled into hard gelatin capsules in 500 mg quantities.

We claim:

1. A method of treating Type I diabetes in a mammal suffering from said disease which comprises administering to such mammal an effective amount of a compound, or a pharmaceutically acceptable salt thereof, of formula (I)

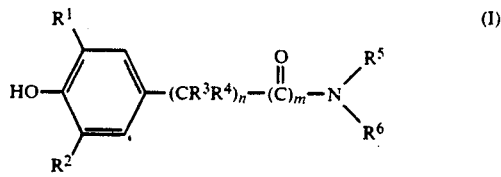

wherein:

$R^1$ and $R^2$ are each independently hydrogen, $C_1$-$C_6$ alkyl, $C_1$-$C_6$ alkoxy or

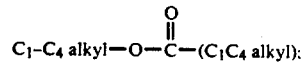

$R^3$ and $R^4$ are each independently hydrogen or $C_1$-$C_4$ alkyl;

n is an integer from 0 to 4, both inclusive;

m is 0 or 1; and $R^5$ and $R^6$ are each independently hydrogen, $C_1$-$C_8$ alkyl, $C_3$-$C_8$ cycloalkyl, $C_2$-$C_8$ alkenyl, $C_2$-$C_8$ alkynyl, $-(CH_2)_qOR^7$, $-(CH_2)_qN(R^7R^8)$, $-(CH_2)_qSR^7$, $-(CH_2)_r$ naphthyl or

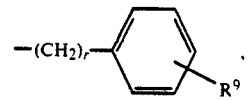

where q is an integer from 1 to 6 both inclusive, $R^7$ and $R^8$ are each independently hydrogen or $C_1$-$C_4$ alkyl, $R^9$ is hydrogen, halo, $C_1$-$C_4$ alkyl, trifluoromethyl, hydroxy, amino, $C_1$-$C_4$ alkylamino, di($C_1$-$C_4$ alkyl)amino, phenylamino or diphenylamino, and r is an integer from 0 to 4, both inclusive.

2. The method of claim 1 which employs a compound of formula I, or a pharmaceutically acceptable salt thereof, wherein $R^1$, $R^2$, $R^3$, $R^4$, $R^5$ and $R^6$ are as defined in claim 1; n is an integer from 0 to 4, both inclusive; and m is 0 or 1; with the proviso that both m and n cannot be zero.

3. The method of claim 2 which employs a compound of formula (I), or a pharmaceutically acceptable salt thereof, wherein $R^1$, $R^2$, $R^3$, $R^4$, m and n are as defined in claim 2 and $R^5$ and $R^6$ are each independently hydrogen, $C_1$-$C_6$ alkyl, $C_2$-$C_6$ alkenyl, $C_2$-$C_6$ alkynyl, $-(CH_2)_qOH$; $-(CH_2)_qNH_2$, $-(CH_2)_qNH(C_1$-$C_4$ alkyl), $-(CH_2)_qN(C_1$-$C_4$ alkyl)$_2$, $-(CH_2)_qS(C_1$-$C_4$ alkyl) or

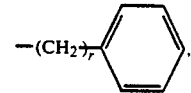

where q is an integer from 1 to 6, both inclusive, and r is an integer from 0 to 4, both inclusive.

4. The method of claim 3 which employs a compound of formula (I), or a pharmaceutically acceptable salt thereof, wherein $R^1$ and $R^2$ are either both 1,1-dimethylethyl or one of $R^1$ and $R^2$ is hydrogen or methyl and the other is 1,1-dimethylethyl, n is an integer from 1 to 4, both inclusive, $R^3$ and $R^4$ are hydrogen, m is 0 and $R^5$ and $R^6$ are each independently hydrogen or $C_1-C_4$ alkyl.

5. The method of claim 3 wherein the compound employed is 4-[(dimethylamino)methyl]-2,6-bis(1,1-dimethylethyl)phenol or a pharmaceutically acceptable salt thereof.

6. The method of claim 5 wherein the pharmaceutically acceptable salt thereof i the hydrochloride salt.

7. The method of claim 3 wherein the compound employed is 4-[(ethylamino)methyl]-2,6-bis(1,1-dimethylethyl)phenol or a pharmaceutically acceptable salt thereof.

8. The method of claim 7 wherein the pharmaceutically acceptable salt thereof is the hydrochloride salt.

* * * * *